(12) United States Patent
Greenhalgh et al.

(10) Patent No.: US 8,067,215 B2
(45) Date of Patent: Nov. 29, 2011

(54) PROCESS OF PRODUCING POLYMERS

(75) Inventors: Stuart Greenhalgh, Smithfield, VA (US); Kenneth Charles Symes, Keighley (GB); Yvonne Armitage, Holmfirth (GB); Jonathan Hughes, Huddersfield (GB); Gary Richardson, Bradford (GB)

(73) Assignee: Ciba Specialty Chemicals Water Treatments Ltd., West Yorkshire, Bradford (GB)

( * ) Notice: Subject to any disclaimer, the term of this patent is extended or adjusted under 35 U.S.C. 154(b) by 533 days.

(21) Appl. No.: 10/580,447

(22) PCT Filed: Nov. 22, 2004

(86) PCT No.: PCT/EP2004/013250
§ 371 (c)(1),
(2), (4) Date: May 23, 2006

(87) PCT Pub. No.: WO2005/054488
PCT Pub. Date: Jun. 16, 2005

(65) Prior Publication Data
US 2007/0184536 A1      Aug. 9, 2007

(30) Foreign Application Priority Data

Dec. 2, 2003 (GB) .................................. 0327901.5

(51) Int. Cl.
*C12P 5/02* (2006.01)
*C12P 1/00* (2006.01)
*C12P 7/62* (2006.01)
*C12P 7/40* (2006.01)
*C12P 5/00* (2006.01)

(52) U.S. Cl. .......... 435/167; 435/41; 435/135; 435/136; 435/166

(58) Field of Classification Search .................. 435/166, 435/167, 170
See application file for complete search history.

(56) References Cited

U.S. PATENT DOCUMENTS

| | | | |
|---|---|---|---|
| 4,343,900 A | 8/1982 | Watanabe et al. | 54/127 |
| 4,506,062 A | 3/1985 | Flesher et al. | 526/211 |
| 4,528,321 A | 7/1985 | Allen et al. | 524/761 |
| 4,599,379 A | 7/1986 | Flesher et al. | 524/801 |
| 5,089,411 A | 2/1992 | Yamada et al. | 435/244 |
| 5,334,519 A * | 8/1994 | Yamada et al. | 435/129 |
| 5,698,629 A | 12/1997 | Seki et al. | 524/827 |
| 5,827,699 A | 10/1998 | Yanenko et al. | 435/129 |
| 6,146,861 A | 11/2000 | Armitage et al. | 435/128 |
| 6,162,624 A | 12/2000 | Symes et al. | 435/135 |
| 6,361,981 B1 | 3/2002 | Symes et al. | 435/135 |
| 7,129,217 B2 | 10/2006 | Murao et al. | 514/23 |
| 2003/0148480 A1 | 8/2003 | Dicosimo et al. | 435/136 |
| 2004/0048297 A1 | 3/2004 | Scherf | 435/170 |
| 2004/0048348 A1 | 3/2004 | Murao et al. | 435/170 |
| 2004/0175810 A1 | 9/2004 | Petersen et al. | 435/128 |
| 2005/0064564 A1 | 3/2005 | Petersen et al. | 435/129 |

FOREIGN PATENT DOCUMENTS

| | | |
|---|---|---|
| EP | 0 102 760 | 3/1984 |
| EP | 0 126 528 | 11/1984 |
| EP | 0 150 933 | 8/1985 |
| EP | 0 307 926 | 3/1989 |
| EP | 0 362 829 | 4/1990 |
| GB | 2 062 625 | 5/1981 |
| SU | 1731814 | 5/1992 |
| WO | 92/05205 | 4/1992 |
| WO | 97/06248 | 2/1997 |
| WO | WO 97/06248 * | 2/1997 |
| WO | 97/21827 | 6/1997 |
| WO | 02/50297 | 6/2002 |
| WO | 02/088371 | 11/2002 |
| WO | 02/088372 | 11/2002 |
| WO | 02/088373 | 11/2002 |
| WO | 03/033716 | 4/2003 |

OTHER PUBLICATIONS

Straathof, A.J.J., 2005, Appl. Microbiol. Biotechnol. 67, 727-734.*
English language abstract of WO 03/033716 from the esp@cenet. com web site printed on Jul. 24, 2006.
Maestracci et al.; Adv. Biochem, Eng. Biotechnol. vol. 36: pp. 104-115(1988).
Bengis-Garber et al.; Appl. Microbiol. Biotechnol. vol. 32: pp. 11-16 (1989).
T. Nagasawa et al.; Pure & Appl. Chem. vol. 67, No. 7, pp. 1241-1256 (1995).
A. Arnaud et al.; Agric. Biol. Chem. vol. 41, (11), pp. 2183-2191 (1977), Abstract only in English.
Y. Asano et al.; Agric. Biol. Chem. vol. 46,(5), pp. 1183-1189 (1982).
T. Nagasawa et al.; Appl. Microbiol Biotechnol vol. 34: pp. 322-324 (1990).
H. Yamada et al.; Biosci. Biotech. Biochem. vol. 60 (9), pp. 1391-1400 (1996).
T. Leonova et al.; Applied Biochemistry and Biotechnology, vol. 88, (2000), pp. 231-241.

* cited by examiner

*Primary Examiner* — Ruth A. Davis
*Assistant Examiner* — Sheridan Macauley
(74) *Attorney, Agent, or Firm* — Shiela A. Loggins

(57) ABSTRACT

A process for preparing a polymer of an ethylenically unsaturated monomer, in which the monomer is obtainable from a biocatalysed reaction or a fermentation process, and wherein the monomer contains cellular material and/or components of a fermentation broth, forming the polymer by polymerizing the ethylenically unsaturated monomer or a monomer mixture comprising the ethylenically unsaturated monomer, wherein there is substantially no removal of the cellular material and/or components of the fermentation broth from the ethylenically unsaturated monomer.

17 Claims, No Drawings

PROCESS OF PRODUCING POLYMERS

PROCESS FOR PRODUCING POLYMERS

The present invention relates to a process for making polymers of ethylenically unsaturated monomers. In particular the invention concerns processes in which the ethylenically unsaturated monomers are manufactured using a biocatalyst.

It is well known to employ biocatalysts, such as microorganisms that contain enzymes, for conducting chemical reactions, or to use enzymes that are free of microorganisms. It is known that various ethylenically unsaturated monomers can be prepared by converting a substrate starting material into the desired monomer by use of a biocatalyst.

Nitrile hydratase enzymes are known to catalyse the hydration of nitriles directly to the corresponding amides. Typically nitrile hydratase enzymes can be synthesized by a variety of microorganisms, for instance microorganisms of the genus *Bacillus*, *Bacteridium*, *Micrococcus*, *Brevibacterium*, *Corynebacterium*, *Pseudomonas*, *Acinetobacter*, *Xanthobacter*, *Streptomyces*, *Rhizobium*, *Klebsiella*, *Enterobacter*, *Erwinia*, *Aeromonas*, *Citrobacter*, *Achromobacter*, *Agrobacterium*, *Pseudonocardia*, *Rhodococcus* and *Comamonas*.

Much has been described that relates to the synthesis of nitrile hydratase within microorganisms. Amaud et al., *Agric. Biol. Chem.* 41: (11) 2183-2191 (1977) describes the characteristics of an enzyme they refer to as 'acetonitrilase' from *Brevibacterium* sp R312 which degrades acetonitrile to acetate via the amide intermediate. Asano et al., *Agric. Biol. Chem.* 46: (5) 1183-1189 (1982) isolated *Pseudomonas chlororaphis* B23 which produced nitrile hydratase to catalyse the conversion of acrylonitrile to acrylamide, generating 400 g/L acrylamide.

Various strains of the *Rhodococcus rhodochrous* species have been found to very effectively produce nitrile hydratase enzyme. EP-0 307 926 describes the culturing of *Rhodococcus rhodochrous*, specifically strain J1 in a culture medium that contains cobalt ions. The nitrile hydratase can be used to hydrate nitriles into amides, and in particular the conversion of 3-cyanopyridine to nicotinamide. In one embodiment an amide is produced in a culture medium of the microorganism in which a substrate nitrile is present. In another embodiment a substrate nitrile is added to the culture medium in which a nitrile hydratase has been accumulated to conduct the hydration reaction. There is also a description of isolating the microorganism cells and supporting them in a suitable carrier, for instance by immobilisation, and then contacting them with a substrate. *Rhodococcus rhodochrous* J1, is also used commercially to manufacture acrylamide monomer from acrylonitrile and this process has been described by Nagasawa and Yamada Pure Appl. Chem. 67: 1241-1256 (1995). EP-A-0362829 describes a method for cultivating bacteria of the species *Rhodococcus rhodochrous* comprising at least one of urea and cobalt ion for preparing the cells of *Rhodococcus rhodochrous* having nitrile hydratase activity. Specifically described is *Rhodococcus rhodochrous* J1.

Leonova et al., Appl. Biochem. Biotechnol. 88: 231-241 (2000) entitled, "Nitrile Hydratase of *Rhodococcus*", describes the growth and synthesis of nitrile hydratase in *Rhodococcus rhodochrous* M8. The NH synthesis of this strain is induced by urea in the medium, which is also used as a nitrogen source for growth by this organism. Cobalt is also required for high nitrile hydratase activity. This literature paper looks at induction and metabolic effects in the main.

Leonova et al., Appl. Biochem. Biotechnol. 88: 231-241 (2000) also states that acrylamide is produced commercially in Russia using *Rhodococcus rhodochrous* M8. Russian patent 1731814 describes *Rhodococcus rhodochrous* strain M8.

*Rhodococcus rhodochrous* strain M33 that produces nitrile hydratase without the need of an inducer such as urea is described in US-A-5827699. This strain of microorganism is a derivative of *Rhodococcus rhodochrous* M8.

The production of acrylamide monomer in particular is desirable via the biocatalytic route. In the review publication by Yamada and Kobayashi Biosci. Biotech. Biochem. 60: (9) 1391-1400 (1996) titled "Nitrile Hydratase and its Application to Industrial Production of Acrylamide" a detailed account of the development of a biocatalytic route to acrylamide is described. Three successively better catalysts and their characteristics for acrylamide production and in particular the third generation catalyst *Rhodococcus rhodochrous* J1 are described in some detail.

It is also known to produce ammonium acrylate directly from acrylonitrile by the action of a nitrilase enzyme. WO-A-9721827 describes producing a concentrated solution of ammonium (meth) acrylate which is substantially free of (meth) acrylonitrile by the enzymic hydrolysis of (meth) acrylonitrile in the presence of water using a nitrilase enzyme which has a Km for (meth) acrylonitrile of below 500 micro moles and Ki for ammonium (meth) acrylate above 100,000 micro moles. The enzyme can be obtained from a *Rhodococcus rhodochrous* microorganism.

Nagasawa et al., Appl. Microbiol. Biotechnol. 34: 322-324 (1990) also describe the use of the nitrilase of *Rhodococcus rhodochrous* J1 for the synthesis of acrylic and methacrylic acid. They looked at the effects of temperature, acrylonitrile concentration and pH conditions on the reaction.

Nitrilase has also been used to catalyse the selective hydrolysis of dinitriles as is described by Bengis-Garber and Gutman in Appl. Microbiol. Biotechnol. 32: 11-16 (1989). Their organism *Rhodococcus rhodochrous* NCIMB 11216 was used to selectively convert in particular fumaronitrile to 3-cyanoacrylic acid.

The use of a combination of nitrile hydratase and amidase has often been described for the formation of carboxylic acid from the corresponding nitrile. For instance US-A-2003/0148480 describes the use of the nitrile hydratase and amidase of Comamonas testosteroni 5-MGAM-4D for the formation of acrylic and methacrylic acid with high yields and specificities being obtained.

It is standard practice to remove the biocatalytic cells from the growth medium before using the biomass to produce the monomers in order to avoid contamination of the monomer by impurities that could adversely affect the successful polymerisation of the monomer.

It is generally accepted that even small quantities of impurities can affect the polymerisation of monomers or prevent polymerization taking place at all. For instance initiating systems used for polymerisation are used in tiny amounts and therefore it would require only small amounts of impurities to inactivate them, stopping or short-stopping the polymerisation. Such impurities may result in branching, cross-linking, chain termination or other effects on the polymer. Although it is known to purposely introduce small quantities of specific substances to induce chain transfer, branching or cross-linking during polymerisation, these substances are introduced in a controlled manner into an otherwise substantially pure monomer in order to bring about a particular molecular structure. Recent developments in polymerisation techniques have made it possible to start from essentially pure monomers and introduce trace amounts of chemical additives to form polymers exhibiting extremely high molecular weights or polymers having a particular molecular structure. Consequently it is possible to provide polymers which exhibit properties that are particularly suitable for specific applications, for instance dewatering of suspended solids to provide improved cake solids or in the field of papermaking improved combination of retention, drainage and formation.

It is known to polymerise ethylenically unsaturated monomers in the presence of a biocatalyst. For instance, it is known from WO-A-92/05205 that polyacrylamides with reduced levels of free acrylamide can be prepared by introducing an amidase enzyme into the monomer mixture prior to polymerisation. In this process the microbial cells containing amidase are separated from the fermentation broth. The amidase biocatalyst is not included in the biocatalytic step that forms the monomer but is added in a separate step. An amidase suspension was used in relatively small quantities such that residual levels of acrylamide in the formed polymer would be removed. The polymerisation process employed relatively high levels of initiator and low molecular weight polymers that were used for soil stabilisation were formed.

WO-A-97/06248 describes a process for the production of high stability amidase or nitrilase using a continuous culture under carbon limitation using a carbon source, which includes, respectively, either an amide or nitrile. The amidase made by this process is effective for converting (meth) acrylamide to ammonium (meth) acrylate, and can for instance be added during or after the polymerisation of acrylamide. Therefore the amidase is combining with (meth) acrylamide monomer in order to form ammonium acrylate monomer, or the amidase is combined with poly (meth) acrylamide in order to convert residual free (meth) acrylamide in the polymers into ammonium (meth) acrylate. There is also disclosure of combining the amidase enzyme and/or microorganism in the polymerisable mixture containing acrylamide and then polymerising to form the polymer and wherein the residual (meth) acrylamide content is reduced. In this process the amidase biocatalyst does not form the monomer to be polymerised but is added in a separate step.

By their very nature impurities tend to be variable and give rise to unexpected and usually undesired effects on the polymer. Even small amounts of such impurities may adversely affect the molecular structure of the polymer and in such circumstances would render the polymer product unsuitable for the intended application.

It is therefore standard practice to avoid the presence of contaminants in monomers to be polymerised in order to prevent changes to the intended molecular structure and properties of the polymer. This is true whether the monomer has been manufactured using a synthetic catalyst or a biocatalyst. However, biological manufacture of monomers presents an increased risk of contamination from cellular material and the fermentation broth.

Contaminants that should normally be avoided include sugars, amino acids, metal salts, and polysaccharides, proteins and other organic products present, either from the medium used to generate the biomass or as spent medium, or as a metabolite from the growing cells or the presence of cellular material itself or degradation products arising from cell lysis and breakdown.

WO-A-02/088372 describes a method and device for producing an aqueous acrylamide solution using a biocatalyst. The process involves a separation method for removing the biocatalyst from the acrylamide product. This method involves the use of a centrifuge and optionally in combination with flocculation to remove the biocatalyst. The biocatalyst is washed with water to remove residual monomer and the water is then used in the next bioconversion reaction.

Maestracci et al., Adv. Biochem. Eng. Biotechnol. 36: 69-115 (1988) describes the use of Brevibacterium sp R312 to convert α-aminonitriles to their corresponding amino acids. The products were separated by well-known techniques including removal of the cells by centrifugation followed by crystallisation.

Nagasawa et al., Appl. Microbiol. Biotechnol. 34: 322-324 (1990) concerns the production of acrylic acid and methacrylic acid using *Rhodococcus rhodochrous* J1 nitrilase. The reaction used whole cells of J1 in a solution of buffer to which acrylonitrile was introduced. This paper reports that 39% acrylic acid was achieved. The reaction mixture was centrifuged to remove the cells and the acrylic acid and methacrylic acid were isolated from the reaction mixture using diethyl ether.

The removal of biocatalyst—that is in the form of microbial cells, either whole cells or part of the cellular material; this could be in the form of disrupted cells and its contents and suspending medium, partially purified enzymes or purified enzymes—and associated fermentation materials however from the monomer requires additional processing which can be costly and time-consuming. Consequently it would be desirable to more cost effectively provide polymer products exhibiting specifically designed features using biologically produced monomer.

According to the present invention we provide a process for preparing a polymer of an ethylenically unsaturated monomer, in which the monomer is obtainable from a biocatalytic or a fermentation process, and wherein the monomer contains cellular material and/or components of a fermentation broth, forming the polymer by polymerising the ethylenically unsaturated monomer or a monomer mixture comprising the ethylenically unsaturated monomer, wherein there is substantially no removal of the cellular material and/or components of the fermentation broth from the ethylenically unsaturated monomer.

Desirably the ethylenically unsaturated monomer can be prepared by biocatalytically converting a suitable substrate that is capable of being converted into the ethylenically unsaturated monomer. Typically the substrate is brought into contact with a biocatalyst and thereby converting the substrate into the ethylenically unsaturated monomer containing the cellular material and optionally components of a fermentation. Alternatively the ethylenically unsaturated monomer can be produced as a product of the fermentation process. The biocatalyst desirably comprises a microorganism and the process can be carried out either inside or outside the cell of the microorganism. In cases where the process is carried out inside the cell, this process may be in the form of a single intracellular enzyme that carries out the biocatalytic step, or the process may form part of a metabolic pathway of the microorganism and thus may involve several biocatalytic steps to generate the ethylenically unsaturated monomer.

We have found that it is possible to manufacture polymers having specifically designed features and properties without the need for removing either the biocatalyst or the fermentation broth. By biocatalyst we mean whole microbial cells containing the biocatalytic activity; partial microbial cells; microbial cell material such as disrupted cells in a suspending medium and its contents; partially purified enzymes and purified enzymes; whole microbial cells or partial microbial cells or enzymes in a fermentation medium; or in another suitable suspending medium such as water or physiologically compatible suspending medium. Hereafter, the term biocatalyst refers to microbial cells and cellular material as described here and to any other form of biocatalyst that is known that constitutes an enzyme and any associated cellular material present with the enzyme that may or may not be required to allow biocatalytic activity. Furthermore, the process enables ethylenically unsaturated monomers to be manufactured using a biocatalyst, which desirably results in high conversion of the substrate compound to form monomer in high yield exhibiting very low concentrations of the substrate compound or by-products. It would be generally expected that the presence of either the biocatalyst or the fermentation broth would have a detrimental effect on the polymerisation and the final polymer product that is formed. However, contrary to these expectations polymerising the monomer in the presence of the biocatalyst or the fermentation broth results in the desired polymers without any impairment.

Therefore, according to the present invention it would be possible to avoid removal of either the biocatalyst or the fermentation broth. Therefore it would be possible to avoid separation of the biocatalyst from the fermentation broth such that the monomer is polymerised in the presence of both the biocatalyst and the fermentation broth. Alternatively, the biocatalyst may be removed from the mixture, for instance by an in-line filter or by centrifugation or by flocculation, such that the monomer is polymerised in the presence of the fermentation broth but substantially in the absence of the biocatalyst. It may also be possible to solely remove the fermentation broth prior to the biocatalyst being used to form the monomer, such that the monomer is polymerised in the presence of biocatalyst. However, it is preferred that neither the biocatalyst nor the fermentation broth be removed from the monomer prior to polymerisation.

Consequently, the process would then avoid the processing step that would be required to remove the biocatalyst from the fermentation broth prior to making monomer of a suitable quality and indeed using the monomer in the manufacture of commercial grade polymers. Furthermore, the process preferably avoids the step of removing the biocatalyst from the monomer prior to polymerisation. In addition the monomer can for instance be produced as a product of a fermentation and the monomer produced in this way does not have to be isolated from the fermentation broth prior to polymerisation.

Consequently the process of the present invention can avoid the need for expensive separation equipment for the removal of the biocatalyst: either microbial whole or fractured cells as described previously, which may be used to remove the catalyst from a fermentation broth or for the removal of the catalyst after the monomer product has been made. Furthermore there would be no need to purify the monomer prior to polymerisation.

The biocatalyst should be capable of converting a substrate into the desired monomer. Generally it would be a microorganism that is capable of generating enzymes suitable for the conversion of interest. Also preferred are microorganisms that include those which provide enzymes that are useful in catalysing the production of itaconic acid, maleic acid and (meth)acrylic acid or salts and derivatives thereof as part of, or in part from their metabolic pathways. For instance this could be a microorganism selected from a wide number of microbial genera. These could include but is not restricted to microorganisms selected from the genus *Bacillus, Bacteridium, Micrococcus, Brevibacterium, Corynebacterium, Pseudomonas, Acinetobacter, Xanthobacter, Streptomyces, Rhizobium, Klebsiella, Enterobacter, Erwinia, Aeromonas, Citrobacter, Achromobacter, Agrobacterium, Pseudonocardia, Rhodococcus, Comamonas, Saccharomyces, Dietzia, Clostridium, Lactobacillus, Escherichia, Agrobacterium, Mycobacterium, Methylophilus, Propionibacterium, Actinobacillus, Megasphaera, Aspergillus, Candida* and *Fusarium*. Additionally those microorganisms that produce monomers by catalysing the substrate compounds lactic acid, 3-hydroxpropionic acid, and glycerol, which are then reacted in further processes to give ethylenically unsaturated monomer could also be used. Other preferred microorganisms include those that are capable of producing enzymes that convert nitriles into the corresponding amides or carboxylic acids. Also preferred are those microorganisms that can produce nitrilase suitable for converting (meth)acrylonitrile to (meth)acrylate, for instance those of the genus *Rhodococcus*. Particularly preferred microorganisms are those that can produce nitrile hydratase suitable for converting (meth) acrylonitrile to (meth) acrylamide, for instance those of the *Rhodococcus* genus, especially the *Rhodococcus rhodochrous* species. A particularly suitable biocatalyst is the novel *Rhodococcus rhodochrous* strain NCIMB 41164 which is described and claimed in our co-filed UK patent application 0327907.2, filed 2 Dec. 2003 which has been allocated case reference number BT/3-22351/P2.

*Rhodococcus rhodochrous* strain NCIMB 41164

1. Origin and Deposition

The strain was isolated by us from soil in Bradford, England and deposited on 5 Mar. 2003 at the National Collection of Industrial and Marine Bacteria (NCIMB), where it was assigned the accession number NCIMB 41164 under the Budapest Treaty.

2. Morphological and Cultural Characteristics
   (1) Polymorphic growth
   (2) Motility: immotile
   (3) Non-spore former
   (4) Gram positive
   (5) Aerobic
   (6) Growth on nutrient agar gives salmon pink round colonies within 48 hours at 30° C.

The biocatalyst comprises cellular material in the form of whole cells or fractured cells or part thereof including semi-purified and purified enzyme preparations and optionally comprises fermentation broth. The cellular material may include any of the constituents of a microbial cell, for instance including cell wall material, cell nucleic acid material (for instance DNA or RNA), cytoplasm or proteins. Generally the amount of cellular material presence in the monomer will be at least 0.001% by weight and usually at least 0.005% by weight.

The fermentation broth may include any of the typical ingredients used for culturing the microorganism and also may include products and by-products produced by the microorganism. Typical components of the fermentation broth include sugars, polysaccharides, proteins, peptides, amino acids, nitrogen sources, inorganic salts, vitamins, growth regulators and enzyme inducers. Specifically this could include monosaccharides or disaccharides as sugars; ammonium salts or other nitrogen sources; inorganic salts such as phosphates, sulphates, magnesium, calcium, sodium and potassium salts; metal compounds; vitamins; and complex fermentation medium components, for example com steep liquor; peptone; yeast extract; organic or inorganic compounds that may be used for specific microbial growth requirements; specific enzyme inducers; and organic acids such as citrate or pyruvate; and any other organic or inorganic compounds that may be required to ensure successful growth of the specific microorganism.

The ethylenically unsaturated monomer may be any such substance that can be prepared biologically from a starting material or specific substance, which is termed a substrate. Desirably the monomer includes ethylenically unsaturated amides, N-substituted amides, carboxylic acids, carboxylic acid salts, carboxylic acid esters, amines including free amines, primary, secondary, tertiary amines and quaternary ammonium compounds. Preferably the monomer is acrylic. Also preferably the ethylenically unsaturated monomer is soluble in water. By soluble in water we mean that the monomer has a solubility of at least 5 g per 100 ml at 25° C. More preferably the ethylenically unsaturated monomer is acrylamide or methacrylamide. Other preferred monomers include itaconic acid (or salts thereof), maleic acid (or salts thereof) and (meth)acrylic acid (or salts and derivatives thereof).

The ethylenically unsaturated monomer can be used in the process alone to form the homopolymer or can be mixed with other ethylenically unsaturated monomers to form a monomer mixture that is polymerised to form a copolymer of the ethylenically unsaturated monomer. Any suitable co-monomer may be used for this purpose. Especially where the ethylenically unsaturated monomer is water-soluble. The co-monomer should desirably be water-soluble or potentially water-soluble, such as anhydrides. Typical co-monomers include (meth) acrylamide, (meth) acrylic acid (or salts), itaconic acid (or salts), maleic acid (or salts), maleic anhydride, vinyl sulfonic acid (or salts), allyl sulfonic acid (or salts), 2-acrylamido-2-methyl propane sulfonic acid (or salts), dimethyl amino ethyl (meth) acrylate (or quaternary ammonium salts), dimethyl amino propyl (meth) acrylamide (or quaternary ammonium salts), N-vinyl pyrrolidone, N-vinyl formamide, vinyl acetate, acrylonitrile, (meth) acrylic esters of $C_{1-30}$ alcohols. The salts of the above stated acid monomers may be of any suitable cation but preferably alkali metal or ammonium salts.

The process of the present invention is particular suitable for preparing high molecular weight water-soluble or water swellable polymers. The polymers may for instance be linear, branched or cross-linked. Preferably the polymers are high molecular weight substantially water-soluble that exhibit an intrinsic viscosity (IV) of at least 3 dl/g (measured using a suspended level viscometer in 1M sodium chloride at 25° C.). Usually the polymers will have intrinsic viscosities of at least 4 dl/g and generally significantly higher, for instance at least 7 or 8 dl/g. In many cases the polymers will have IV's of at least 10 or 12 dl/g and could be as high as 20 or 30 dl/g.

The water-soluble or water-swellable polymer prepared according to the process of the present invention may be cationic, anionic, non-ionic or amphoteric. It may be substantially linear or alternatively branched or cross-linked. Cross-linked or branched polymers are prepared by incorporating a branching or cross-linking agent into the monomer blend. The cross-linking or branching agent may be for instance a di- or multifunctional material that reacts with functional groups pendant on the polymer chain, for instance multivalent metal ions or amine compounds which can react with pendant carboxylic groups. Preferably, however, the cross-linking or branching agent will be a poly-ethylenically unsaturated compound, which becomes polymerised into two or more polymer chains. Typically such cross-linking agents include methylene-bis-acrylamide, tetra allyl ammonium chloride, triallyl amine and polyethylene glycol di acrylate. The polymers may be highly crosslinked and therefore water insoluble but water swellable. Alternatively the polymer may be water soluble and either substantially linear or slightly branched, for instance prepared using less than 10 ppm cross-linking/ branching monomer.

Particularly preferred polymers made by the process of the invention include homopolymers or copolymers of acrylamide or methacrylamide. Desirably the copolymers include any of the above stated co-monomers but preferably it is a copolymer of acrylamide with sodium acrylate or a copolymer of acrylamide with quaternary ammonium and acid salts of dimethylaminoethyl(meth)acrylate. Especially preferred acrylamide homo or copolymers are of high molecular weight and exhibit high intrinsic viscosity as defined above.

The polymer is generally formed by subjecting the ethylenically unsaturated monomer or a monomer mixture comprising the ethylenically unsaturated monomer to polymerisation conditions. This may be achieved by heating or irradiation, for instance using ultraviolet light. Preferably polymerisation initiators are introduced into the monomer or mixture of monomers to initiate polymerisation. Desirably this may be achieved by the use of redox initiators and/or thermal initiators. Typically redox initiators include a reducing agent such as sodium sulphite, sulphur dioxide and an oxidising compound such as ammonium persulphate or a suitable peroxy compound, such as tertiary butyl hydroperoxide etc. Redox initiation may employ up to 10,000 ppm (based on weight of monomer) of each component of the redox couple. Preferably though each component of the redox couple is often less than 1000 ppm, typically in the range 1 to 100 ppm, normally in the range 4 to 50 ppm. The ratio of reducing agent to oxidizing agent may be from 10:1 to 1:10, preferably in the range 5:1 to 1:5, more preferably 2:1 to 1:2, for instance around 1:1.

Polymerisation may also be effected by employing a thermal initiator alone or in combination with other initiator systems, for instance redox initiators. Thermal initiators would include any suitable initiator compound that releases radicals at an elevated temperature, for instance azo compounds, such as azobisisobutyronitrile (AZDN), 4,4'-azobis-(4cyanovalereic acid) (ACVA). Typically thermal initiators are used in an amount of up 10,000 ppm, based on weight of monomer. In most cases, however, thermal initiators are used in the range 100 to 5,000 ppm preferably 200 to 2,000 ppm, usually around 1,000 ppm.

Typically an aqueous solution of water soluble monomer may be polymerised by solution polymerisation to provide an aqueous gel or by reverse phase polymerisation in which an aqueous solution of monomer is suspended in a water immiscible liquid and polymerised to form polymeric beads or alternatively by emulsifying aqueous monomer into an organic liquid and then effecting polymerisation. Examples of reverse phase polymerisation are given in EP-A-150933, EP-A-102760 or EP-A-126528.

In a further aspect of the invention the ethylenically unsaturated monomer can be produced by the biocatalyst, optionally mixed with other monomers, and then polymerised in situ to form the polymer. Consequently the ethylenically unsaturated monomer may be produced and then polymerised in the same vessel. Thus the ethylenically unsaturated monomer is produced from the substrate in a vessel, optionally other monomers are introduced into the vessel to form a monomer mixture. The ethylenically unsaturated monomer or monomer mixture is then subjected to polymerisation conditions, optionally by introducing initiators into the vessel, and thereby forming the polymer inside the vessel. Furthermore, the process can be more conveniently adapted by producing the biocatalyst in the same vessel, introducing the substrate into the vessel which is then converted into the ethylenically saturated monomer and then polymerised in the same vessel to form the polymer as defined above.

Thus the process of the present invention provides the advantages of avoiding the need for removing the cells, cellular material or proteinaceous material from the catalytic broth or to remove impurities or cellular material from the monomer. Additionally the product made by this process is a novel composition.

The following examples illustrate the invention.

EXAMPLE 1

(1) *Pseudomonas florescens*, *Saccharomyces cerevisiae* and *Aspergillus terreus* are cultured in nutrient broth at 30° C. until they reach the late exponential phase of growth. The resulting culture broth is centrifuged to remove the biomass and leave a supernatant.

(2) A 25% acrylamide solution is prepared. 10 ppm Sodium hypophosphite and 1000 ppm tertiary-butyl hydrogen peroxide solution is added to the solution. The pH is adjusted to 4.0 using acetic acid. The solution is degassed and 1000 ppm ferrous ammonium sulphate solution is added after which time a polymer is formed.

(3) The procedure in (2) is repeated using supernatant from the culture of the organisms described in (1) to make up the acrylamide solution rather than water. The molecular weight of the resulting solution polymers is measured and compared with a polymer which had been prepared using water to make up the acrylamide solution. The results are shown in Table 1. The molecular weights of the polymers were all virtually the same.

TABLE 1

| Microrganism for supernatant source | Molecular weight |
| --- | --- |
| Control (none) | 245,600 |
| Pseudomonas fluorescens | 231,700 |
| Saccharomyces cerevisiae | 243,600 |
| Aspergillus terreus | 248,100 |

EXAMPLE 2

(1) *Rhodococcus rhodochrous* NCIMB 41164 is grown in a 280 L fermenter containing 180 L culture medium containing the following constituents (g/L): dipotassium hydrogen phosphate 0.7; potassium hydrogen phosphate 0.3; glucose 1.0; urea, 5.0; yeast extract 3.0; magnesium sulphate heptahydrate 0.5; cobalt chloride hexahydrate 0.01;. The pH of the medium is adjusted to pH 7.2. The culture is grown at 30° C. for 3 days. Glucose is also fed to the culture periodically.

The nitrile hydratase activity of the fermentation broth is measured 15 h after harvesting and it is found to be 242,000 U/g at 25° C. (700,000 U/L). (2) 15 L of the fermentation broth from (1) is mixed with 35 L process water, this suspension is then charged to a 600 L reactor that contained 250 kg water. Acrylonitrile is fed to the reactor over a period of several hours until an acrylamide concentration of 46.8% is achieved. 25 kg of the acrylamide solution is centrifuged to remove the biocatalyst. 25 kg of the acrylamide was not centrifuged to remove the biocatalyst.

(3) The centrifuged and non-centrifuged acrylamide samples from (2) are polymerized as homo-polymers using redox and thermal initiators to give gel polymers with IV of approx. 17 dl/g. The viscosity in cP is also measured and there is no difference in the samples prepared using both centrifuged and uncentrifuged acrylamide. The results of the viscosity measurements of the polymers (cP) are shown in Table 2

TABLE 2

| | Viscosity (cP) | | | | |
| --- | --- | --- | --- | --- | --- |
| Centrifuged acrylamide | Standard 28 | Batch 1 32 | Batch 2 37 | Batch 3 28 | Batch 4 27 |
| Acrylamide containing fermentation broth | Standard 28 | Batch 5 29 | Batch 6 28 | Batch 7 27 | Batch 8 26 |

The viscosity specification is 25-40 cP at shear rate 250 s$^{-1}$ (4) The polymers prepared in (3) are tested as flocculants at doses of 16-28 mg/l using 4% china clay at pH 2 as a substrate. The settlement rates are shown in Table 3. No differences in the polymer performances are observed when comparing with the specification for the standard acrylamide sample.

TABLE 3

| Batch number | Settlement Rate (cm/min) Polymer Dose (mg/l) | | | |
| --- | --- | --- | --- | --- |
| | 16 | 20 | 24 | 28 |
| Standard | 35.5 | 42.2 | 49.2 | 56.2 |
| 2 | 30.4 | 39.2 | 45.3 | 50.8 |
| 3 | 36.6 | 39.5 | 53.3 | 60.0 |
| 5 | 43.6 | 46.6 | 56.4 | 70.6 |
| 7 | 31.0 | 36.0 | 43.4 | 43.8 |

EXAMPLE 3

A 30% (w/w) acrylamide solution containing up to 20% by weight of fermentation broth of microorganism *Rhodococcus rhodochrous* NCIMB 41164 is prepared. The acrylamide doped with fermentation broth is polymerized as a homopolymer using redox and thermal initiators to form a gel polymer with IV of approx 17 dl/g. The results of the 1 point IV viscosity measurements for each of the polymer solutions are shown in Table 4. The viscosity results are all within the specification set for this polymer.

TABLE 4

| Fermentation Broth Concentration | IV (dl/g) |
| --- | --- |
| 0 | 16.9 |
| 5 | 16.5 |
| 10 | 17.6 |
| 15 | 17.2 |
| 20 | 17.9 |

The invention claimed is:
1. A process for preparing a polymer of an ethylenically unsaturated monomer, in which the monomer is obtained from a biocatalysed reaction or a fermentation process, and wherein the monomer contains cellular material and/or components of a fermentation broth, forming the polymer by polymerising the ethylenically unsaturated monomer or a monomer mixture comprising the ethylenically unsaturated monomer and cellular material and/or components of a fermentation broth in the presence of a redox and/or thermal initiator and the formed polymer exhibits an intrinsic viscosity of at least 3 dl/g measured using a suspended level viscometer in 1 M sodium chloride at 25° C.

2. A process according to claim 1 in which the ethylenically unsaturated monomer is prepared by providing a substrate that can be converted into the ethylenically unsaturated monomer, contacting the substrate with a biocatalyst which biocatalyst comprises a microorganism or cellular material and thereby converting the substrate into the ethylenically unsaturated monomer containing the cellular material and/or components of a fermentation broth and this process is carried out inside or outside of the cell and where it is carried out inside the cell it optionally forms part of a metabolic pathway of the microorganism.

3. A process according to claim 2 in which the biocatalyst comprises a microorganism and wherein the process is carried out inside the cell and forms part of a metabolic process of the microorganism.

4. A process according to claim 1 in which the cellular material comprises whole cells.

5. A process according to claim 1 in which the cellular material comprises fractured cellular material.

6. A process according to claim 5 in which the fractured cellular material is selected from the group consisting of cell wall material, cell membrane material, cell nucleus material, cytoplasm and proteins.

7. A process according to claim 1 in which the components of the fermentation broth are selected from the group consisting of sugars, polysaccharides, proteins, peptides, amino acids, nitrogen sources, inorganic salts (including metal salts), vitamins, growth regulators, enzyme inducers and complex fermentation medium components.

8. A process according to claim 1 in which the ethylenically unsaturated monomer is (meth)acrylamide monomer.

9. A process according to claim 2 in which the substrate is (meth)acrylonitrile.

10. A process according to claim 2 in which the biocatalyst comprises a nitrile hydratase enzyme.

11. A process according to claim 1 in which the polymer is a homopolymer or copolymer of (meth) acrylamide.

12. A process according to claim 1 in which the ethylenically unsaturated monomer is selected from the group consisting of itaconic acid (or salts thereof), maleic acid (or salts thereof) and (meth) acrylic acid (or salts or derivatives thereof).

13. A process according to claim 2 in which the substrate is introduced into a vessel and contacted with a biocatalyst and wherein the substrate is converted into the ethylenically unsaturated monomer, optionally introducing other monomers into the vessel to form a monomer mixture, subjecting the ethylenically unsaturated monomer or monomer mixture to polymerisation conditions, optionally by introducing initiators into the vessel, and thereby forming the polymer inside the vessel.

14. A process according to claim 13 in which the biocatalyst is produced in the vessel.

15. A process according to claim 2 in which the biocatalyst comprises microorganisms of the *Rhodococcus* genus.

16. A process according to claim 15 in which the microorganism is *Rhodococcus rhodochrous* NCIMB 41164.

17. A composition comprising a polymer of an ethylenically unsaturated monomer and further comprising cellular material and/or components of a fermentation broth, wherein the composition is obtained by a process according to claim 1.

* * * * *